United States Patent
Ridler

(10) Patent No.: US 12,355,271 B2
(45) Date of Patent: *Jul. 8, 2025

(54) MAGNETIC FIELD CANCELLATION CIRCUITRY

(71) Applicant: Cochlear Limited, Macquarie University (AU)

(72) Inventor: Oliver John Ridler, Cherrybrook (AU)

(73) Assignee: Cochlear Limited, Macquarie University (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/427,595

(22) Filed: Jan. 30, 2024

(65) Prior Publication Data

US 2024/0171015 A1 May 23, 2024

Related U.S. Application Data

(63) Continuation of application No. 17/757,025, filed as application No. PCT/IB2020/061597 on Dec. 7, 2020, now Pat. No. 11,923,700.

(60) Provisional application No. 62/958,151, filed on Jan. 7, 2020.

(51) Int. Cl.
| | |
|---|---|
| H02J 50/70 | (2016.01) |
| A61N 1/08 | (2006.01) |
| A61N 1/36 | (2006.01) |
| H02J 50/10 | (2016.01) |
| H04B 5/26 | (2024.01) |
| H04B 5/79 | (2024.01) |

(52) U.S. Cl.
CPC ............... *H02J 50/70* (2016.02); *A61N 1/08* (2013.01); *A61N 1/36038* (2017.08); *H02J 50/10* (2016.02); *H04B 5/26* (2024.01); *H04B 5/79* (2024.01); *H02J 2310/23* (2020.01)

(58) Field of Classification Search
CPC ....................................................... H02J 50/70
USPC ........................................................ 307/104
See application file for complete search history.

(56) References Cited

U.S. PATENT DOCUMENTS

| | | |
|---|---|---|
| 5,630,835 A | 5/1997 | Brownlee |
| 5,741,315 A | 4/1998 | Lee et al. |
| 6,298,271 B1 | 10/2001 | Weijand |
| 8,577,474 B2 | 11/2013 | Rahman et al. |

(Continued)

OTHER PUBLICATIONS

Int'l Search Report and Written Opinion for PCT/IB2020/061597 filed Dec. 7, 2020, dated Mar. 11, 2021.

*Primary Examiner* — Joseph Chang
(74) *Attorney, Agent, or Firm* — Knobbe, Martens, Olson & Bear, LLP

(57) ABSTRACT

An apparatus includes at least one first circuit configured to generate a first time-varying magnetic field for magnetic induction power transfer to a device, at least one second circuit configured to generate and/or receive a second time-varying magnetic field for magnetic induction data transfer to and/or from the device, and at least one third circuit configured to generate a third time-varying magnetic field in response to a time-varying electric current. The third time-varying magnetic field is configured to at least partially inhibit degradation of said data transfer from the first time-varying magnetic field. The apparatus further includes at least one fourth circuit configured to generate the time-varying electric current in response to a received portion of the first time-varying magnetic field.

22 Claims, 9 Drawing Sheets

(56) References Cited

U.S. PATENT DOCUMENTS

| | | | |
|---|---|---|---|
| 11,923,700 B2 * | 3/2024 | Ridler | A61N 1/08 |
| 2011/0112610 A1 | 11/2011 | Rahman et al. | |
| 2012/0109256 A1 | 5/2012 | Meskins et al. | |
| 2014/0246916 A1 | 9/2014 | Von Novak | |
| 2016/0038739 A1 | 2/2016 | Liu | |
| 2018/0028824 A1 | 2/2018 | Pivonka et al. | |
| 2020/0064920 A1 | 2/2020 | Soltani et al. | |

* cited by examiner

MAGNETIC FIELD CANCELLATION CIRCUITRY

CLAIM OF PRIORITY

The present application is a continuation of U.S. patent application Ser. No. 17/757,025 filed Jun. 8, 2022 which is a U.S. national stage filing of PCT Appl. No. PCT/IB2020/061597 filed Dec. 7, 2020 which claims the benefit of priority to U.S. Provisional Appl. No. 62/958,151 filed Jan. 7, 2020, each of which is incorporated in its entirety by reference herein.

BACKGROUND

Field

The present application relates generally to systems and methods for facilitating wireless power and data transmission, and more specifically, for facilitating wireless power and data transmission between an external portion and an implanted portion of an implanted medical system.

Description of the Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In one aspect disclosed herein, an apparatus comprises at least one first circuit configured to generate a first time-varying magnetic field for magnetic induction power transfer to a device. The apparatus further comprises at least one second circuit configured to generate and/or receive a second time-varying magnetic field for magnetic induction data transfer to and/or from the device. The apparatus further comprises at least one third circuit configured to generate a third time-varying magnetic field in response to a time-varying electric current, the third time-varying magnetic field configured to at least partially inhibit degradation of said data transfer from the first time-varying magnetic field. The apparatus further comprises at least one fourth circuit configured to generate the time-varying electric current in response to a received portion of the first time-varying magnetic field.

In another aspect disclosed herein, a method comprises transferring power via a first magnetic induction link in a first region. The method further comprises transferring data via a second magnetic induction link in a second region, said transferring data simultaneous with said transferring power. The method further comprises generating an electric current indicative of a first magnetic field from said first magnetic induction link. The method further comprises, in response to the electric current, generating a second magnetic field in the second region in opposition to at least a portion of the first magnetic field within the second region.

In another aspect disclosed herein, an apparatus comprises magnetic induction power transfer circuitry configured to generate an induction power transfer magnetic field. The apparatus further comprises at least one circuit that is sensitive to the induction power transfer magnetic field. The apparatus further comprises protection circuitry configured to generate a protection magnetic field in response to an electric current. The protection magnetic field is configured to at least partially protect the at least one circuit from the induction power transfer magnetic field. The apparatus further comprises circuitry configured to generate the electric current in response to the induction power transfer magnetic field or in response to a signal indicative of the induction power transfer magnetic field.

BRIEF DESCRIPTION OF THE DRAWINGS

Implementations are described herein in conjunction with the accompanying drawings, in which.

DETAILED DESCRIPTION

Figure 1:
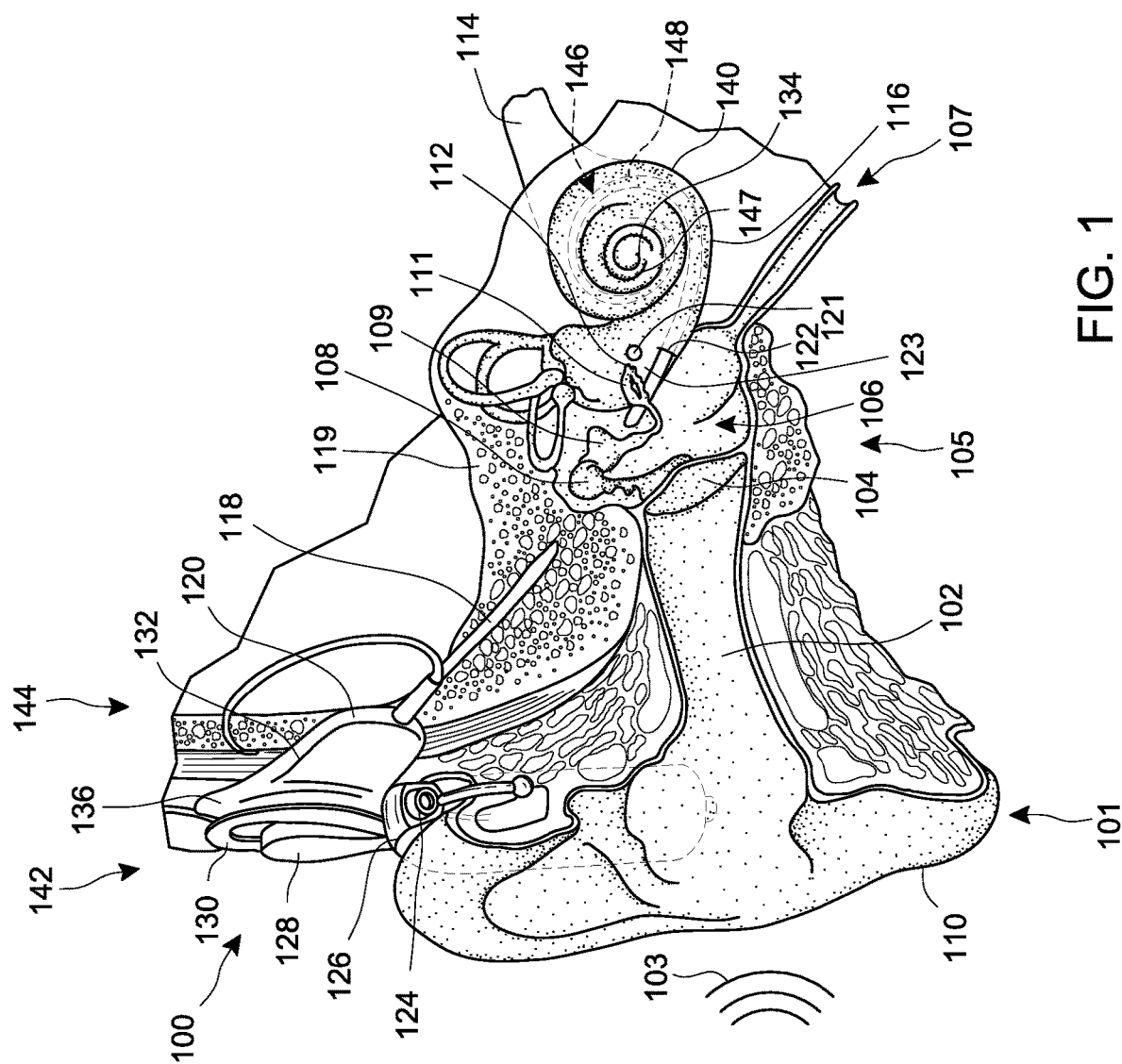
FIG. 1 is a perspective view of an example cochlear implant auditory prosthesis implanted in a recipient in accordance with certain implementations described herein.

In certain systems, magnetic induction power transfer is performed concurrently and in close proximity to other low-power operations which can experience degradation due to the large time-varying magnetic fields involved in the magnetic induction power transfer. For example, an external portion of an auditory prosthesis can utilize magnetic induction to provide power transcutaneously to an implanted portion of the auditory prosthesis while also using magnetic induction to communicate data transcutaneously with the implanted portion. Due to the relatively small size of the external portion (e.g., an over-the-ear or button sound processor), the low-power magnetic induction data transfer link can experience excessive noise and other interference due to the concurrent operation of the nearby high-power magnetic induction power transfer link. For another example, signals from an electromagnetic microphone of the external portion of the auditory prosthesis can be disrupted by the concurrent operation of the nearby high-power magnetic induction power transfer link to the implanted portion.

Certain implementations described herein comprise cancellation circuitry configured to generate a magnetic field configured to destructively interfere with (e.g., counteract; in opposition to) the portion of the large time-varying magnetic field in the region of the circuitry performing the low-power operation, thereby at least partially inhibiting the degradation of the low-power operation. In certain implementations, the cancellation circuitry is powered by magnetic induction from at least one pick-up coil receiving a portion of the large time-varying magnetic field (e.g., passively powered). In certain other implementations, the cancellation circuitry is powered by a separate power supply in response to a sensor signal indicative of the large time-varying magnetic field (e.g., actively powered).

The teachings detailed herein are applicable, in at least some implementations, to any type of implantable medical device (e.g., implantable sensory prostheses) comprising a first portion (e.g., external to a recipient) and a second portion (e.g., implanted on or within the recipient), the first portion configured to wirelessly transmit power to the second portion and to wirelessly communicate with the second portion. For example, the implantable medical device can comprise an auditory prosthesis system utilizing an external sound processor configured to transcutaneously provide power and data (e.g., control signals) to an implanted assembly (e.g., comprising an actuator) that generates stimulation signals that are perceived by the recipient as sounds. Examples of auditory prosthesis systems compatible with certain implementations described herein include but are not limited to: electro-acoustic electrical/acoustic systems, cochlear implant devices, implantable hearing aid devices, middle ear implant devices, Direct Acoustic Cochlear Implant (DACI), middle ear transducer (MET), electro-acoustic implant devices, other types of auditory prosthesis devices, and/or combinations or variations thereof, or any other suitable hearing prosthesis system with or without one or more external components. Implementations can include any type of medical device that can utilize the teachings detailed herein and/or variations thereof.

Merely for ease of description, apparatus and methods disclosed herein are primarily described with reference to an illustrative medical device, namely a cochlear implant. However, the teachings detailed herein and/or variations thereof may also be used with a variety of other medical devices that provide a wide range of therapeutic benefits to recipients, patients, or other users. In some implementations, the teachings detailed herein and/or variations thereof can be utilized in other types of implantable medical devices beyond auditory prostheses. For example, apparatus and methods disclosed herein and/or variations thereof may also be used with one or more of the following: vestibular devices (e.g., vestibular implants); visual devices (e.g., bionic eyes); visual prostheses (e.g., retinal implants); sensors; cardiac pacemakers; drug delivery systems; defibrillators; functional electrical stimulation devices; catheters; brain implants; seizure devices (e.g., devices for monitoring and/or treating epileptic events); sleep apnea devices; electroporation; etc. The concepts described herein and/or variations thereof can be applied to any of a variety of implantable medical devices comprising an implanted component configured to use magnetic induction to communicate transcutaneously with an external component (e.g., receive control signals from the external component and/or transmit sensor signals to the external component) while using magnetic induction to receive power from the external component. In still other implementations, the teachings detailed herein and/or variations thereof can be utilized in other types of systems beyond medical devices utilizing magnetic induction for both wireless power transfer and data communication. For example, such other systems can include one or more of the following: consumer products (e.g., smartphones; IoT devices) and electric vehicles (e.g., automobiles).

FIG. 1 is a perspective view of an example cochlear implant auditory prosthesis 100 implanted in a recipient in accordance with certain implementations described herein. The example auditory prosthesis 100 is shown in FIG. 1 as comprising an implanted stimulator unit 120 (e.g., an actuator) and an external microphone assembly 124 (e.g., a partially implantable cochlear implant). An example auditory prosthesis 100 (e.g., a totally implantable cochlear implant) in accordance with certain implementations described herein can replace the external microphone assembly 124 shown in FIG. 1 with a subcutaneously implantable assembly comprising an acoustic transducer (e.g., microphone), as described more fully herein.

As shown in FIG. 1, the recipient normally has an outer ear 101, a middle ear 105, and an inner ear 107. In a fully functional ear, the outer ear 101 comprises an auricle 110 and an ear canal 102. An acoustic pressure or sound wave 103 is collected by the auricle 110 and is channeled into and through the ear canal 102. Disposed across the distal end of the ear canal 102 is a tympanic membrane 104 which vibrates in response to the sound wave 103. This vibration is coupled to oval window or fenestra ovalis 112 through three bones of middle ear 105, collectively referred to as the ossicles 106 and comprising the malleus 108, the incus 109, and the stapes 111. The bones 108, 109, and 111 of the middle ear 105 serve to filter and amplify the sound wave 103, causing the oval window 112 to articulate, or vibrate in response to vibration of the tympanic membrane 104. This vibration sets up waves of fluid motion of the perilymph within the cochlea 140. Such fluid motion, in turn, activates tiny hair cells (not shown) inside the cochlea 140. Activation of the hair cells causes appropriate nerve impulses to be generated and transferred through the spiral ganglion cells (not shown) and auditory nerve 114 to the brain (also not shown) where they are perceived as sound.

As shown in FIG. 1, the example auditory prosthesis 100 comprises one or more components which are temporarily or permanently implanted in the recipient. The example auditory prosthesis 100 is shown in FIG. 1 with an external component 142 which is directly or indirectly attached to the recipient's body, and an internal component 144 which is temporarily or permanently implanted in the recipient (e.g., positioned in a recess of the temporal bone adjacent auricle 110 of the recipient). The external component 142 typically comprises one or more input elements/devices for receiving input signals at a sound processing unit 126. The one or more input elements/devices can include one or more sound input elements (e.g., one or more external microphones 124)

for detecting sound and/or one or more auxiliary input devices (not shown in FIG. 1) (e.g., audio ports, such as a Direct Audio Input (DAI); data ports, such as a Universal Serial Bus (USB) port; cable ports, etc.). In the example of FIG. 1, the sound processing unit 126 is a behind-the-ear (BTE) sound processing unit configured to be attached to, and worn adjacent to, the recipient's ear. However, in certain other implementations, the sound processing unit 126 has other arrangements, such as by an OTE processing unit (e.g., a component having a generally cylindrical shape and which is configured to be magnetically coupled to the recipient's head), a mini or micro-BTE unit, an in-the-canal unit that is configured to be located in the recipient's ear canal, a body-worn sound processing unit, etc.

The sound processing unit 126 of certain implementations includes a power source (not shown in FIG. 1) (e.g., battery), a processing module (not shown in FIG. 1) (e.g., comprising one or more digital signal processors (DSPs), one or more microcontroller cores, one or more application-specific integrated circuits (ASICs), firmware, software, etc. arranged to perform signal processing operations), and an external transmitter unit 128. In the illustrative implementation of FIG. 1, the external transmitter unit 128 comprises circuitry that includes at least one external inductive communication coil 130 (e.g., a wire antenna coil comprising multiple turns of electrically insulated single-strand or multi-strand platinum or gold wire). The external transmitter unit 128 also generally comprises a magnet (not shown in FIG. 1) secured directly or indirectly to the at least one external inductive communication coil 130. The at least one external inductive communication coil 130 of the external transmitter unit 128 is part of an inductive radio frequency (RF) communication link with the internal component 144. The sound processing unit 126 processes the signals from the input elements/devices (e.g., microphone 124 that is positioned externally to the recipient's body, in the depicted implementation of FIG. 1, by the recipient's auricle 110). The sound processing unit 126 generates encoded signals, sometimes referred to herein as encoded data signals, which are provided to the external transmitter unit 128 (e.g., via a cable). As will be appreciated, the sound processing unit 126 can utilize digital processing techniques to provide frequency shaping, amplification, compression, and other signal conditioning, including conditioning based on recipient-specific fitting parameters.

The power source of the external component 142 is configured to provide power to the auditory prosthesis 100, where the auditory prosthesis 100 includes a battery (e.g., located in the internal component 144, or disposed in a separate implanted location) that is recharged by the power provided from the external component 142 (e.g., via a transcutaneous energy transfer link). The transcutaneous energy transfer link is used to transfer power and/or data to the internal component 144 of the auditory prosthesis 100. Various types of energy transfer, such as infrared (IR), electromagnetic, capacitive, and inductive transfer, may be used to transfer the power and/or data from the external component 142 to the internal component 144. During operation of the auditory prosthesis 100, the power stored by the rechargeable battery is distributed to the various other implanted components as needed.

The internal component 144 comprises an internal receiver unit 132, a stimulator unit 120, and an elongate stimulation assembly 118. In some implementations, the internal receiver unit 132 and the stimulator unit 120 are hermetically sealed within a biocompatible housing, sometimes collectively referred to as a stimulator/receiver unit.

The internal receiver unit 132 comprises at least one internal inductive communication coil 136 (e.g., a wire antenna coil comprising multiple turns of electrically insulated single-strand or multi-strand platinum or gold wire), and generally, a magnet (not shown in FIG. 1) fixed relative to the at least one internal inductive communication coil 136. The at least one internal inductive communication coil 136 receives power and/or data signals from the at least one external inductive communication coil 130 via a transcutaneous energy transfer link (e.g., an inductive RF link). The stimulator unit 120 generates stimulation signals (e.g., electrical stimulation signals; optical stimulation signals) based on the data signals, and the stimulation signals are delivered to the recipient via the elongate stimulation assembly 118.

The elongate stimulation assembly 118 has a proximal end connected to the stimulator unit 120, and a distal end implanted in the cochlea 140. The stimulation assembly 118 extends from the stimulator unit 120 to the cochlea 140 through the mastoid bone 119. In some embodiments, the stimulation assembly 118 can be implanted at least in the basal region 116, and sometimes further. For example, the stimulation assembly 118 can extend towards an apical end of the cochlea 140, referred to as the cochlea apex 134. In certain circumstances, the stimulation assembly 118 can be inserted into the cochlea 140 via a cochleostomy 122. In other circumstances, a cochleostomy can be formed through the round window 121, the oval window 112, the promontory 123, or through an apical turn 147 of the cochlea 140.

The elongate stimulation assembly 118 comprises a longitudinally aligned and distally extending array 146 (e.g., electrode array; contact array) of stimulation elements 148 (e.g., electrical electrodes; electrical contacts; optical emitters; optical contacts). The stimulation elements 148 are longitudinally spaced from one another along a length of the elongate body of the stimulation assembly 118. For example, the stimulation assembly 118 can comprise an array 146 comprising twenty-two (22) stimulation elements 148 that are configured to deliver stimulation to the cochlea 140. Although the array 146 of stimulation elements 148 can be disposed on the stimulation assembly 118, in most practical applications, the array 146 is integrated into the stimulation assembly 118 (e.g., the stimulation elements 148 of the array 146 are disposed in the stimulation assembly 118). As noted, the stimulator unit 120 generates stimulation signals (e.g., electrical signals; optical signals) which are applied by the stimulation elements 148 to the cochlea 140, thereby stimulating the auditory nerve 114.

While FIG. 1 schematically illustrates an auditory prosthesis 100 utilizing an external component 142 comprising an external microphone 124, an external sound processing unit 126, and an external power source, in certain other implementations, one or more of the microphone 124, sound processing unit 126, and power source are implantable on or within the recipient (e.g., within the internal component 144). For example, the auditory prosthesis 100 can have each of the microphone 124, sound processing unit 126, and power source implantable on or within the recipient (e.g., encapsulated within a biocompatible assembly located subcutaneously), and can be referred to as a totally implantable cochlear implant ("TICI"). For another example, the auditory prosthesis 100 can have most components of the cochlear implant (e.g., excluding the microphone, which can be an in-the-car-canal microphone) implantable on or within the recipient, and can be referred to as a mostly implantable cochlear implant ("MICI").

FIGS. 2A-2G schematically illustrate planar projection views of various example apparatus 200 in accordance with certain implementations described herein. The apparatus 200 comprises at least one first circuit 210 configured to generate a first time-varying magnetic field 212 for magnetic induction power transfer to a device. The apparatus 200 further comprises at least one second circuit 220 configured to generate and/or receive a second time-varying magnetic field (not shown) for magnetic induction data transfer to and/or from the device. The apparatus 200 further comprises at least one third circuit 230 configured to generate a third time-varying magnetic field 232 in response to a time-varying electric current 242. The third time-varying magnetic field 232 is configured to at least partially inhibit degradation of said data transfer from the first time-varying magnetic field 212. The apparatus 200 further comprises at least one fourth circuit 240 configured to generate the time-varying electric current 242 in response to a received portion of the first time-varying magnetic field 212 or in response to a signal indicative of the first time-varying magnetic field 212.

In certain implementations, the apparatus 200 is an external portion of a medical system (e.g., a portion of the medical system that is not implanted on or within the recipient) and the device comprises an implanted portion of the medical system (e.g., a portion implanted on or within a recipient). For example, the apparatus 200 can comprise an external portion (e.g., a sound processing unit 126) of an auditory prosthesis 100 (e.g., a cochlear implant system). As schematically illustrated by FIGS. 2A-2G, the apparatus 200 of certain implementations comprises a housing 250 (e.g., polymer; plastic) configured to be worn externally by the recipient and containing the at least one first circuit 210, the at least one second circuit 220, the at least one third circuit 230, and the at least one fourth circuit 240. The housing 250 of certain implementations is configured to further contain at least one power source (e.g., battery) and processing circuitry configured to receive and process data signals to be communicated to the implanted portion of the medical device via the at least one second circuit 220. For example, for an auditory prosthesis 100, the processing circuitry can be configured to process data signals received from a microphone 124 and to generate encoded data signals (e.g., utilizing digital processing techniques for frequency shaping, amplification, compression, and/or other signal conditioning, including conditioning based on recipient-specific fitting parameters) which are provided to the implanted portion of the auditory prosthesis 100 via the at least one second circuit 220.

Figure 2A:
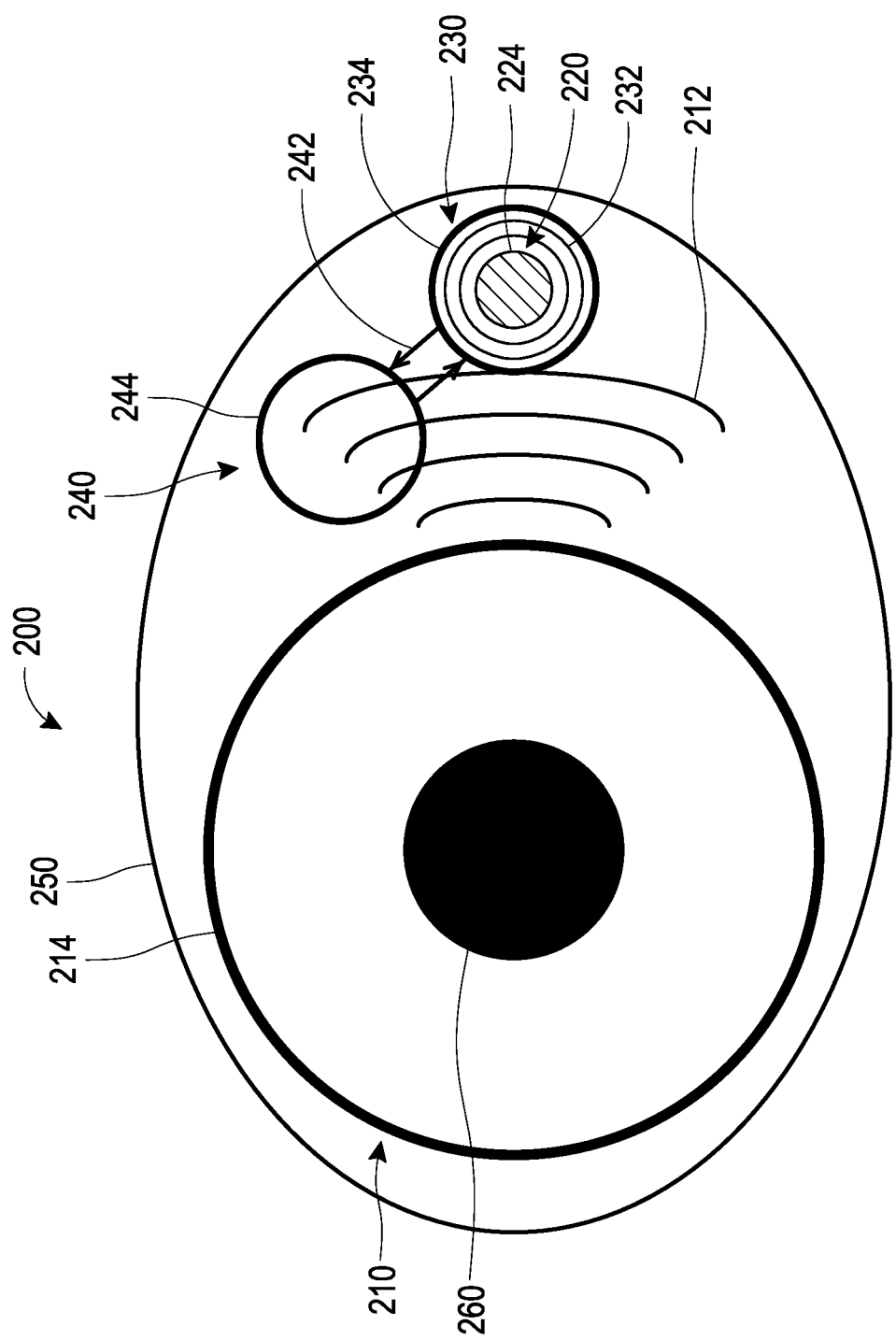
FIGS. 2A-2G schematically illustrate planar projection views of various example apparatus in accordance with certain implementations described herein.

The housing 250 of certain implementations is configured to be held in place externally to the recipient during power transfer (e.g., using the at least one first circuit 210) and data transfer (e.g., using the at least one second circuit 220). For example, as schematically illustrated by FIG. 2A, the apparatus 200 can further comprise at least one magnet 260 (e.g., within the housing 250). The at least one magnet 260 can be configured to create an attractive magnetic force with a corresponding magnetic material (e.g., a magnet) of the implanted portion of the medical system, the attractive magnetic force configured to hold the apparatus 200 in an operative position relative to the implanted portion. When the apparatus 200 is in the operative position, the at least one first circuit 210 forms a magnetic inductive RF power transfer link (e.g., for transcutaneous power transfer) with corresponding circuitry of the implanted portion, and the at least one second circuit 220 forms a magnetic inductive RF data transfer link (e.g., for transcutaneous data transfer) with corresponding circuitry of the implanted portion.

In certain implementations, the at least one first circuit 210 comprises at least one electrically conductive power transfer coil 214 configured to be operationally coupled by magnetic induction to the corresponding circuitry (e.g., at least one electrically conductive power transfer coil) of the implanted portion. For example, the power transfer coil 214 can comprise an electrically conductive conduit (e.g., wire; conductive trace on a printed circuit board). The at least one power transfer coil 214 is configured to receive a time-varying electric current (e.g., from controller circuitry of the apparatus 200) and to generate the first time-varying magnetic field 212 (e.g., an inductive power transfer magnetic field) that transfers power via magnetic induction to the corresponding circuitry of the implanted portion. In certain implementations, the first time-varying (e.g., alternating) magnetic field 212 has a frequency in a range of 100 kHz to 100 MHz (e.g., 5 MHz; 6.78 MHz; 12 MHz; 49 MHZ). In certain implementations in which the apparatus 200 comprises an external portion of a medical system, the power transfer is in a range of 1 mW to 500 mW. In certain other implementations, the power transfer in a range of 1 W to 1 KW (e.g., for consumer devices; for IoT devices) or in a range of 1 kW to 100 KW (e.g., for vehicles).

In certain implementations, the power transfer coil 214 of the at least one first circuit 210 has one or more (e.g., 2, 3, 4, 5, or more) windings, a generally planar, generally circular shape (e.g., having an inner diameter in a range of 10 mm to 50 mm), and bounds a region having an area in a range of 70 mm$^2$ to 850 mm$^2$. Other shapes (e.g., non-planar; elliptical; square; rectangular; polygonal; geometric; irregular; symmetric; non-symmetric) and sizes of the power transfer coil 214 are also compatible with certain implementations described herein. FIG. 2A shows the power transfer coil 214 encircling the magnet 260 (e.g., the magnet 260 and the power transfer coil 214 are substantially concentric and/or substantially planar with one another; the magnet 260 having a projection in a projection plane that is within a projection of the power transfer coil 214 in the projection plane). In certain other implementations, the power transfer coil 214 is positioned at other positions (e.g., alongside; non-concentric) relative to the magnet 260.

In certain implementations, the at least one second circuit 220 comprises at least one antenna 224 configured to be operationally coupled by magnetic induction to the corresponding circuitry (e.g., at least one antenna) of the implanted portion. The at least one antenna 224 is configured to transmit data to the corresponding circuitry via the second time-varying magnetic field (e.g., by generating a data-encoded time-varying magnetic field in response to a data-encoded time-varying electric signal from controller circuitry of the apparatus 200) and/or to receive data from the corresponding circuitry via the second time-varying magnetic field (e.g., by receiving a data-encoded time-varying magnetic field from the corresponding circuitry and generating a data-encoded time-varying electric signal that is provided to the controller circuitry of the apparatus 200). For example, the at least one antenna 224 can comprise an electrically conductive conduit (e.g., a conductive coil having an axis and wound around a ferrite rod having a length that is in a range of 4 mm to 10 mm and a diameter in a range of 1.5 mm to 3 mm; a conductive coil having an axis and wound around an air-filled region). In certain implementations, the data-encoded time-varying (e.g., alternating) magnetic field generated or received by the at least one second circuit 220 has a frequency (e.g., in a range of 10 MHz to 20 MHZ) and the power of the data transfer is orders of magnitude less than the power transferred by the at least one first circuit 210 (e.g., the power of the data transfer is on the order of nW or µW).

In certain implementations, the at least one third circuit 230 comprises at least one cancellation coil 234 in proximity to the at least one antenna 224 of the at least one second circuit 220 (e.g., the cancellation coil 234 bounds a region containing the antenna 224). For example, the cancellation coil 234 can comprise an electrically conductive conduit (e.g., wire; conductive trace on a printed circuit board). As schematically illustrated by FIG. 2A, the cancellation coil 234 can encircle the antenna 224 (e.g., the antenna 224 and the cancellation coil 234 are substantially concentric and/or substantially planar with one another; the antenna 224 has a projection in a projection plane that is within a projection of the cancellation coil 234 in the projection plane) and each of the antenna 224 and the cancellation coil 234 are outside a region bounded by the power transfer coil 214 (e.g., each of the antenna 224 and the cancellation coil 234 has a projection in a projection plane that is outside a projection of the power transfer coil 214 in the projection plane). In certain implementations, the cancellation coil 234 has one or more (e.g., 2, 3, 4, 5, or more) windings, a generally planar, generally circular shape (e.g., having an inner diameter in a range of 2 mm to 20 mm), and bounds a region having an area in a range of 3 mm$^2$ to 300 mm$^2$. Other shapes (e.g., non-planar; elliptical; square; rectangular; polygonal; geometric; irregular; symmetric; non-symmetric) and sizes of the cancellation coil 234 are also compatible with certain implementations described herein. In certain implementations in which the antenna 224 comprises a conductive coil having an axis and wound around either a ferrite rod or an air-filled region, the antenna 224 can be positioned with the axis of the antenna 224 perpendicular to an axis of the cancellation coil 234 (e.g., the axis of the antenna 224 parallel to a printed circuit board on which the cancellation coil 234 is formed).

In certain implementations, the at least one cancellation coil 234 is configured to generate the third time-varying magnetic field 232 (e.g., a protection magnetic field) in response to a time-varying electric current 242 received by the at least one cancellation circuit 234 from the at least one fourth circuit 240. The third time-varying magnetic field 232 is configured to at least partially inhibit (e.g., reduce; cancel; prevent; avoid; minimize) degradation of the data transfer between the at least one second circuit 220 and the corresponding circuitry of the implanted portion, the degradation due to the first time-varying magnetic field 212 from the at least one first circuit 210. For example, the third time-varying magnetic field 232 is configured to be in opposition to (e.g., to be in opposite phase with) at least a portion of the first time-varying magnetic field 212 such that the third time-varying magnetic field 232 destructively interferes with at least the portion of the first time-varying magnetic field 212 within the region bounded by the at least one cancellation coil 234 (e.g., at the at least one antenna 224 of the at least one second circuit 220).

In certain implementations, the destructive interference of the first time-varying magnetic field 212 within the region by the third time-varying magnetic field 232 at least partially reduces (e.g., counteracts; opposes; cancels; minimizes) a magnitude of the superposition of the first and third time-varying magnetic fields 212, 232 (e.g., net magnetic field) within the region bounded by the at least one cancellation coil 234. For example, the third time-varying magnetic field 232 can have a substantially opposite phase to that of the first time-varying magnetic field 212 and can have a magnitude at the antenna 224 that is substantially equal to the magnitude of the first time-varying magnetic field 212 at the antenna 224 (e.g., substantially total destructive interference at the antenna 224; complete cancellation at the antenna 224; substantially zero net magnetic field). In certain implementations, the third time-varying magnetic field 232 at the antenna 224 has a magnitude in at least one direction (e.g., substantially perpendicular to the plane of the cancellation coil 234) that is substantially equal and opposite to the magnitude of the first time-varying magnetic field 212 at the antenna 224 in the at least one direction (e.g., such that the net magnetic field from the superposition of the first and third time-varying magnetic fields 212, 232 in the direction substantially perpendicular to the plane of the cancellation coil 234 is substantially zero).

In certain implementations, examples of which are schematically illustrated in FIGS. 2A-2F, the at least one fourth circuit 240 comprises at least one pick-up coil 244 in series electrical communication with the at least one third circuit 230. For example, the at least one pick-up coil 244 can comprise an electrically conductive conduit (e.g., wire; conductive trace on a printed circuit board). As schematically illustrated by FIGS. 2A-2F, the at least one pick-up coil 244 can be in series electrical communication with the cancellation coil 234 of the at least one third circuit 230. The at least one pick-up coil 244 is configured to generate (e.g., passively) the time-varying electric current 242 via magnetic induction resulting from the received portion of the first time-varying magnetic field 212 and to provide the time-varying electric current 242 to the cancellation coil 234. For example, the at least one pick-up coil 244 can be spaced away from the cancellation coil 234 and in electrical communication with the cancellation coil 234 via electrically conductive conduits (e.g., wires; conductive traces on a printed circuit board).

In certain implementations, the pick-up coil 244 has one or more (e.g., 2, 3, 4, 5, or more) windings, a generally planar, generally circular shape (e.g., having an inner diameter in a range of 2 mm to 50 mm), and bounds a region having an area in a range of 3 mm$^2$ to 850 mm$^2$. Other shapes (e.g., non-planar; elliptical; square; rectangular; polygonal; geometric; irregular; symmetric; non-symmetric) and sizes of the pick-up coil 244 are also compatible with certain implementations described herein.

As described by Lenz's law, a changing magnetic field will induce currents to flow within a conductor exposed to the changing magnetic field, the currents generating secondary magnetic fields that oppose the changing magnetic field. Therefore, a cancellation coil 234 exposed to the first time-varying magnetic field 212 will generate magnetic fields that oppose the first time-varying magnetic field 212 within the cancellation coil 234. However, due to the resistance and imperfections of the cancellation coil 234, this opposition is only partial and the first time-varying magnetic field 212 is only partially canceled by the secondary magnetic fields generated by the induced currents in the cancellation coil 234.

In certain implementations, the at least one pick-up coil 244 is configured to generate and provide sufficient electric current to the cancellation coil 234 such that the cancellation coil 234 generates the third time-varying magnetic field 232 with sufficient magnitude to produce a predetermined reduction of a magnitude of the superposition of the first and third time-varying magnetic fields 212, 232 within the region bounded by the cancellation coil 234. In certain such implementations, the characteristics of the at least one cancellation coil 234 and/or the at least one pick-up coil 244 are selected such that the at least one cancellation coil 234 generates the third time-varying magnetic field 232 in response to the electric current from the at least one pick-up coil 244 (e.g., the electric current magnetically induced in the at least one pick-up coil 244 by the first time-varying magnetic field 212 is greater than the electric current magnetically induced in the cancellation coil 234 by the first time-varying magnetic field 212). Examples of such characteristics include but are not limited to one or more of the following: the relative positions of the cancellation coil 234 and the pick-up coil 244 relative to the power transfer coil 212 (e.g., which determine the magnitudes of the time-varying magnetic field 212 at the cancellation coil 234 and at the pick-up coil 244); the sizes (e.g., areas) of the cancellation coil 234 and/or the pick-up coil 244; and the number of windings of the cancellation coil 234 and/or the pick-up coil 244. Various example implementations are schematically shown in FIGS. 2A-2F, which are described below in reference to the equations (e.g., for planar coils) for magnetic flux: $\Phi(t) = \oint B(t)dA \cong NAB(t)$ and magnetically induced current:

$$I(t) = \frac{1}{R}\frac{d\Phi(t)}{dt},$$

where $\Phi(t)$ is the time-varying magnetic flux flowing through the area of the coil, B(t) is the time-varying magnetic field at the coil, R is the resistance of the coil, N is the number of windings of the coil, and A is the area of the coil.

For example, as schematically illustrated by FIG. 2A, the pick-up coil 244 is outside a region encircled by the at least one power transfer coil 214 (e.g., the pick-up coil 244 has a projection in a projection plane that is outside a projection of the power transfer coil 214 in the projection plane), and the pick-up coil 244 and the cancellation coil 234 have substantially equal areas (e.g., substantially equal shapes and sizes) and numbers of windings, and the pick-up coil 244 is positioned closer to the power transfer coil 214 than is the cancellation coil 234 (e.g., a distance between the centers of the pick-up coil 244 and the power transfer coil 214 is less than a distance between the centers of the cancellation coil 234 and the power transfer coil 214). Because the pick-up coil 244 is closer to the power transfer coil 214, the magnitude of the portion of the first time-varying magnetic field 212 B(t) flowing through the area A of the pick-up coil 244 is greater than the magnitude of the portion of the first time-varying magnetic field 212 B(t) flowing through the area A of the cancellation coil 234, such that the cumulative electric current I(t) flowing through the cancellation coil 234 generates the third time-varying magnetic field 232.

Figure 2C:
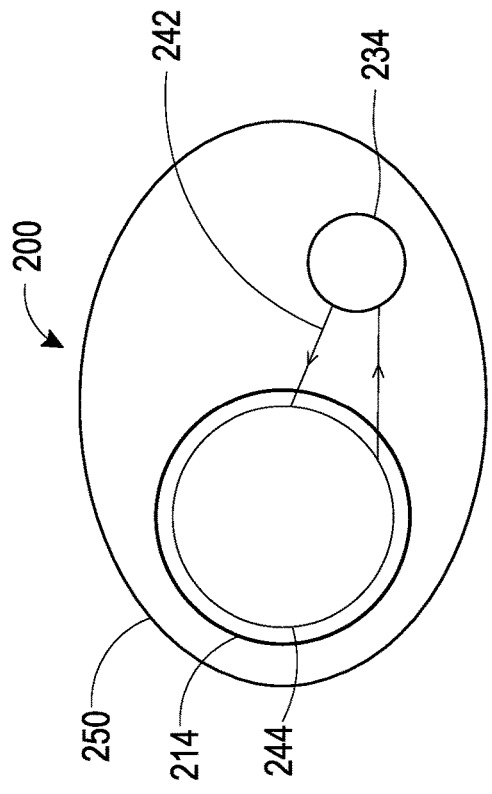
Figure 2G:
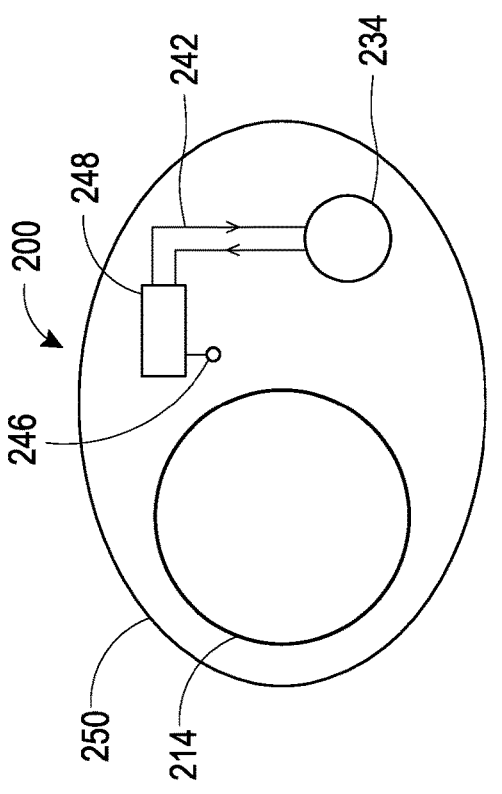
Figure 2B:
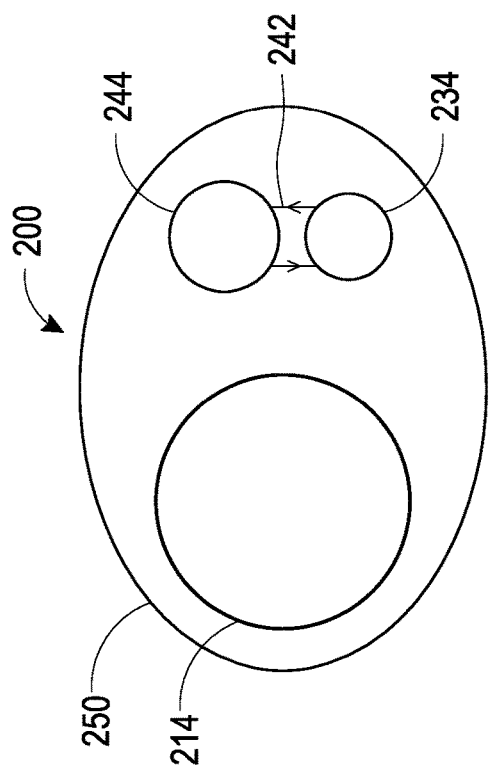

For another example, as schematically illustrated by FIG. 2B, the pick-up coil 244 is outside a region encircled by the at least one power transfer coil 214 (e.g., the pick-up coil 244 has a projection in a projection plane that is outside a projection of the power transfer coil 214 in the projection plane), and the pick-up coil 244 is positioned at a substantially equal distance from the power transfer coil 214 as is the cancellation coil 234 (e.g., the distance between the centers of the pick-up coil 244 and the power transfer coil 214 is substantially equal to the distance between the centers of the cancellation coil 234 and the power transfer coil 214), but the pick-up coil 244 has a larger area A and/or a larger number of windings N than does the cancellation coil 234.

For another example, as schematically illustrated by FIG. 2C, the pick-up coil 244 is within a region encircled by the at least one power transfer coil 214 (e.g., the pick-up coil 244 and the power transfer coil 214 are substantially concentric and/or substantially planar with one another; the pick-up coil 244 has a projection in a projection plane that is within a projection of the power transfer coil 214 in the projection plane). Because the pick-up coil 244 is within the inner area of the power transfer coil 214, the magnitude of the time-varying magnetic flux from the portion of the first time-varying magnetic field 212 flowing through the area of the pick-up coil 244 is greater than the magnitude of the time-varying magnetic flux from the portion of the first time-varying magnetic field 212 flowing through the area of the cancellation coil 234, such that the electric current flowing through the cancellation coil 234 generates the third time-varying magnetic field 232.

Figure 2D:
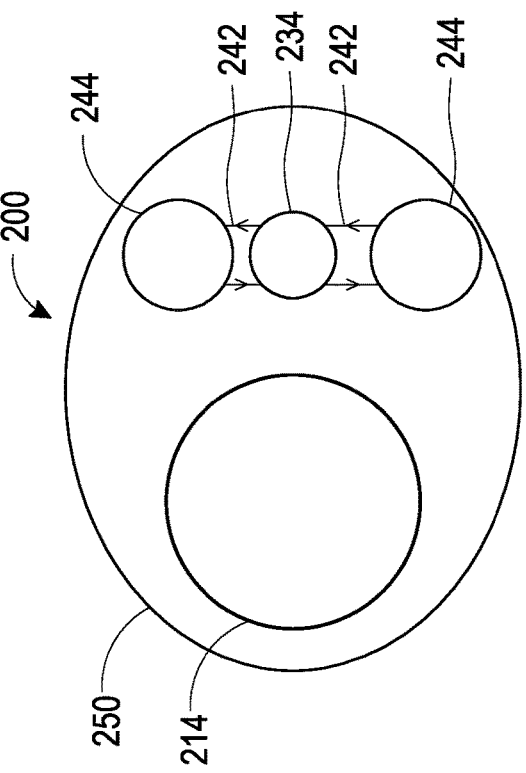

For another example, as schematically illustrated by FIG. 2D, the at least one pick-up coil 244 comprises a plurality of pick-up coils 244 in series electrical communication with the cancellation coil 234, spaced away from the cancellation coil 234 and one another, and outside a region encircled by the at least one power transfer coil 214 (e.g., the pick-up coils 244 have projections in a projection plane that are outside a projection of the power transfer coil 214 in the projection plane). Because the cumulative areas A of the pick-up coils 244 is greater than the area A of the cancellation coil 234, the magnitude of the time-varying magnetic flux from the portion of the first time-varying magnetic field 212 flowing through the cumulative areas of the pick-up coil 244 is greater than the magnitude of the time-varying magnetic flux from the portion of the first time-varying magnetic field 212 flowing through the area of the cancellation coil 234, such that the electric current flowing through the cancellation coil 234 generates the third time-varying magnetic field 232.

Figure 2E:
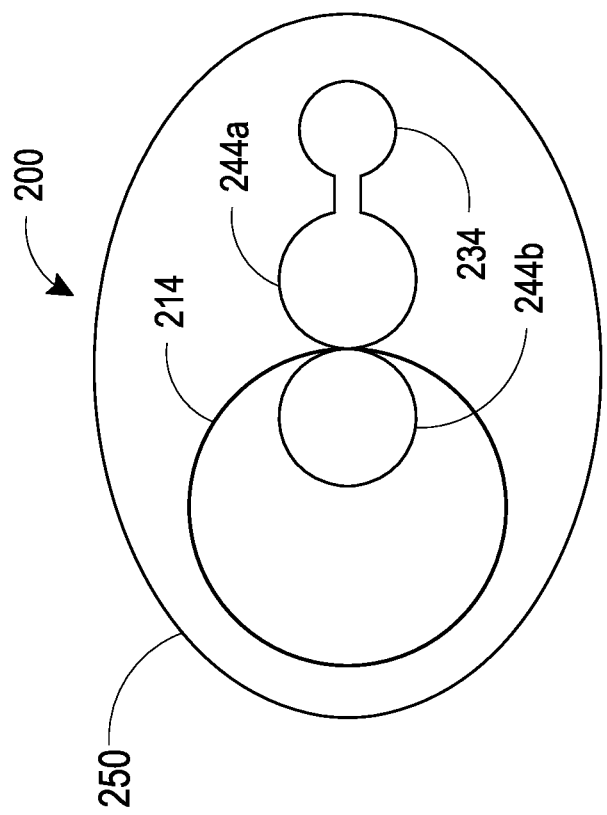

For another example, as schematically illustrated by FIG. 2E, the pick-up coil 244 is outside a region encircled by the at least one power transfer coil 214 (e.g., the pick-up coil 244 has a projection in a projection plane that is outside a projection of the power transfer coil 214 in the projection plane), is closer to the at least one power transfer coil 214 than is the cancellation coil 234, and has a larger area and/or a larger number of windings than does the cancellation coil 234.

Figure 2F:
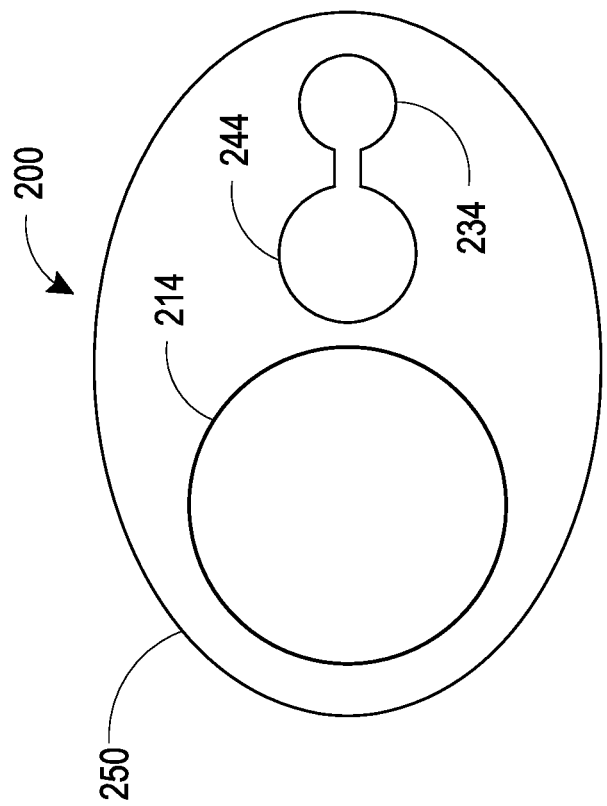

For another example, as schematically illustrated by FIG. 2F, the at least one pick-up coil 244 comprises a pair of pick-up coils 244*a*, 244*b* in series electrical communication with one another and with the cancellation coil 234. A first pick-up coil 244*a* is outside a region encircled by the at least one power transfer coil 214 (e.g., the first pick-up coil 244*a* has a projection in a projection plane that is outside a projection of the power transfer coil 214 in the projection plane) and a second pick-up coil 244*b* is inside the region encircled by the at least one power transfer coil 214 (e.g., the second pick-up coil 244*b* has a projection in a projection plane that is inside a projection of the power transfer coil 214 in the projection plane). In certain implementations, the area of the first pick-up coil 244*a* and the area of the second pick-up coil 244*b* are substantially equal to one another and/or the number of windings of the first pick-up coil 244*a* and the number of windings of the second pick-up coil 244*b* are substantially equal to one another. The direction of the magnetic field within the first pick-up coil 244*a* is substantially opposite to the direction of the magnetic field within the second pick-up coil 244*b* since the first pick-up coil 244*a* is within the region encircled by the power transfer coil 214 and the second pick-up coil 244*b* is outside the region encircled by the power transfer coil 214. The first pick-up coil 244a and the second pick-up coil 244b have a cross-over portion therebetween to compensate for these different directions of the magnetic fields, such that the electrical current induced in one of the first and second pick-up coils 244a, 244b is in the clockwise direction and the electrical current induced in the other of the first and second pick-up coils 244a, 244b is in the counterclockwise direction (e.g., the two electrical currents do not oppose one another when provided to the cancellation coil 234).

Figure 3:
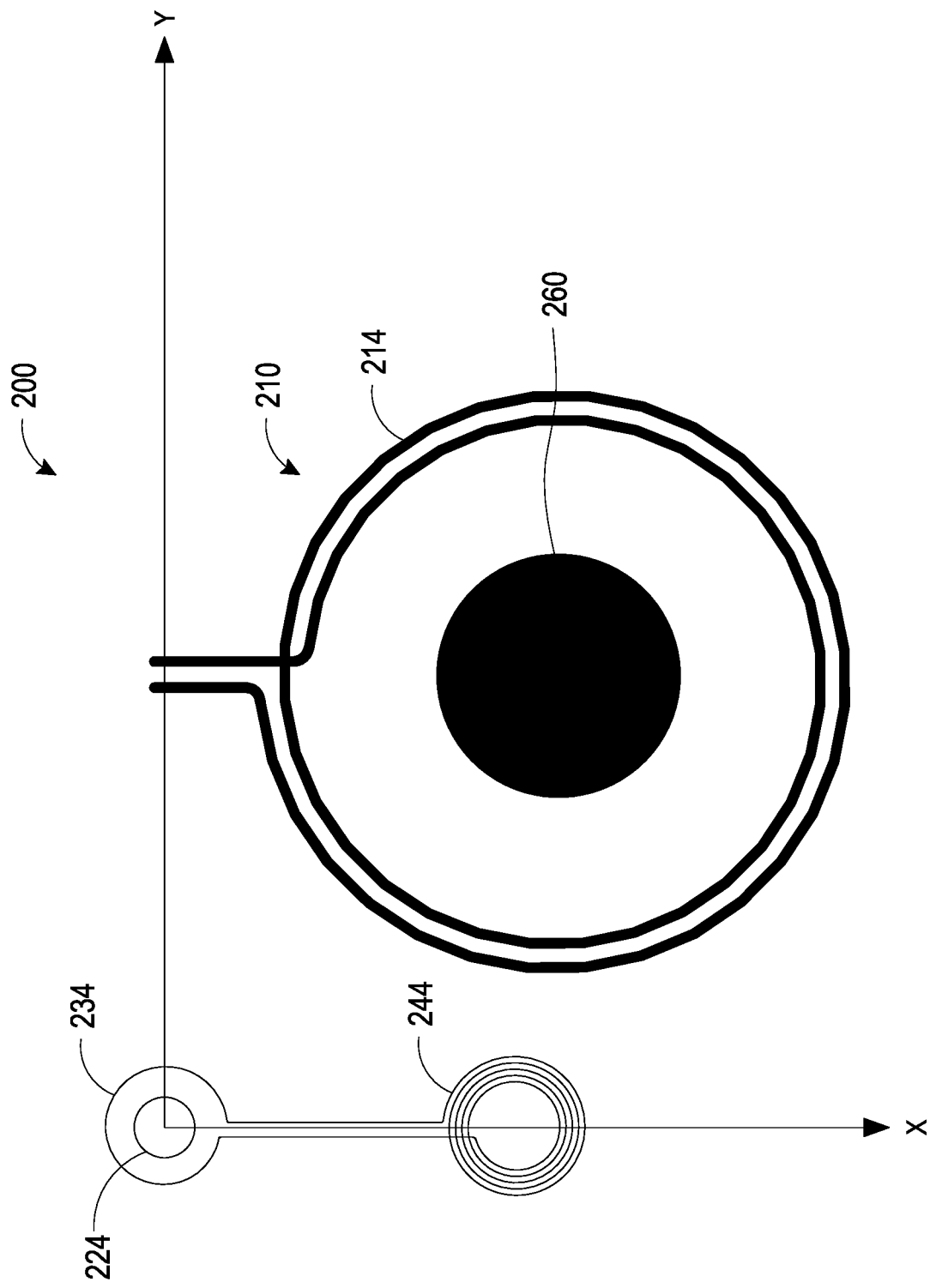
FIG. 3 schematically illustrates an example apparatus in accordance with certain implementations described herein.

FIG. 3 schematically illustrates an example apparatus 200 in accordance with certain implementations described herein. The apparatus 200 of FIG. 3 comprises a first circuit 210 comprising a power transfer coil 214, a second circuit 220 comprising an antenna 224, a third circuit 230 comprising a cancellation coil 234, and a fourth circuit 240 comprising a pick-up coil 244. The power transfer coil 214 of FIG. 3 encircles the magnet 260, and the pick-up coil 244 of FIG. 3 comprises multiple windings while the cancellation coil 234 comprises a single winding. In addition, each of the power transfer coil 214, the cancellation coil 234, and the pick-up coil 244 is substantially planar and are substantially planar with one another (e.g., each of the coils 214, 234, 244 are substantially in the X-Y plane). In certain other implementations, two or more of the power transfer coil 214, the cancellation coil 234, and the pick-up coil 244 are not substantially planar with one another and/or are not substantially planar with one another (e.g., are spaced above or below the X-Y plane).

Figure 4A:
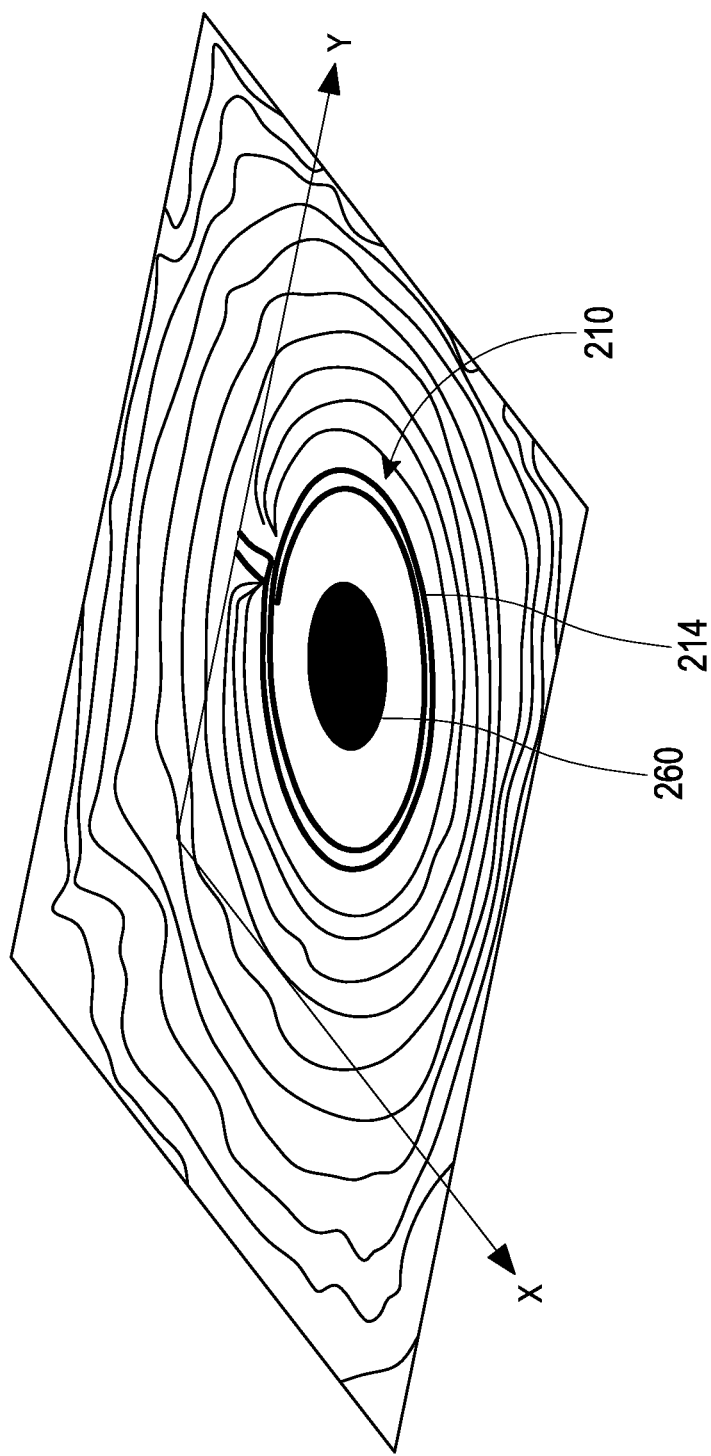
FIG. 4A schematically illustrates a calculation of the first time-varying magnetic field generated by the power transfer coil without either the cancellation coil or the pick-up coil.
Figure 4B:
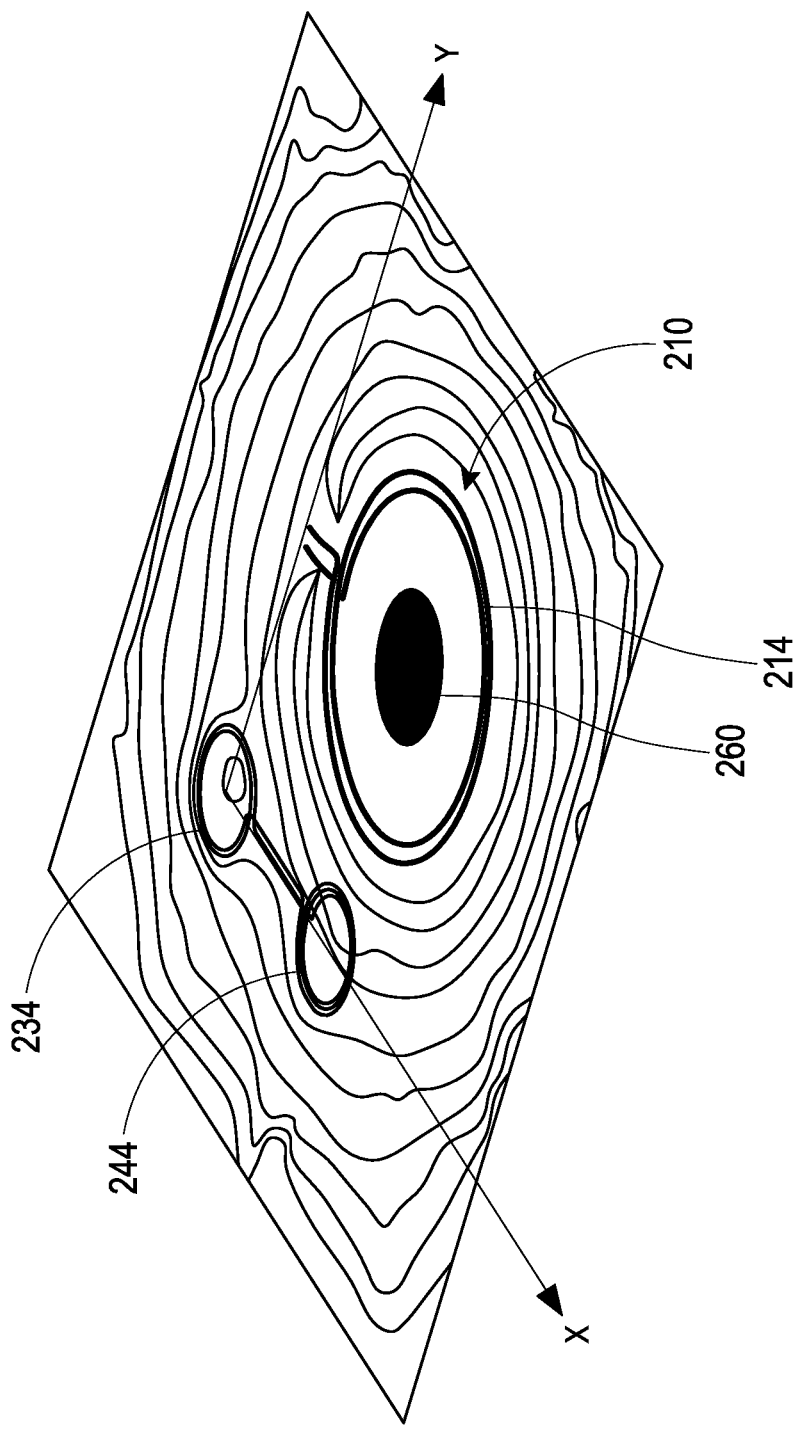
FIG. 4B schematically illustrates a calculation of the superposition of the first time-varying magnetic field generated by the power transfer coil and the third time-varying magnetic field with both the cancellation coil and the pick-up coil in accordance with certain implementations described herein.

FIG. 4A schematically illustrates a calculation of the first time-varying magnetic field 212 generated by the power transfer coil 214 without either the cancellation coil 234 or the pick-up coil 244. The lines generally encircling the power transfer coil 214 represent different magnitudes of the first time-varying magnetic field 212 along the Z direction (perpendicular to the X-Y plane) generated by the power transfer coil 214 in the X-Y plane. FIG. 4B schematically illustrates a calculation of the superposition of the first time-varying magnetic field 212 generated by the power transfer coil 214 and the third time-varying magnetic field 232 with both the cancellation coil 234 and the pick-up coil 244 in accordance with certain implementations described herein. A comparison of FIGS. 4A and 4B illustrates that the magnitudes along the Z direction of the superposition of the first time-varying magnetic field 212 and the third time-varying magnetic field 232 in the region of the antenna 224 within the area bounded by the cancellation coil 234 is reduced by the cancellation coil 234 and the pick-up coil 244.

In certain implementation, an example of which is schematically illustrated in FIG. 2E, the at least one fourth circuit 240 comprises at least one sensor 246 and control circuitry 248 (e.g., a microprocessor; an application-specific integrated circuit; an amplifier) in series electrical communication with the at least one third circuit 230 (e.g., the cancellation coil 234). The at least one sensor 246 can comprise a sensor coil comprising an electrically conductive conduit (e.g., wire; conductive trace on a printed circuit board), the sensor coil configured to generate (e.g., passively) a sensor signal via magnetic induction resulting from the received portion of the first time-varying magnetic field 212. The sensor signal is generated in response to the first time-varying magnetic field 212 at the at least one sensor 246, and is indicative of the first time-varying magnetic field 212. The control circuitry 248 is configured to respond to the sensor signal by generating (e.g., actively) the time-varying electric current 242, which is indicative of the first time-varying magnetic field 212 at the at least one second circuit 220. In certain implementations, the control circuitry 248 is configured to receive electrical power from the same power source of the apparatus 200 that powers the at least one first circuit 210, while in certain other implementations, the control circuitry 248 further comprise a separate power source (e.g., a battery) from which the control circuitry 248 receives electrical power. For example, the control circuitry 248 can determine, in response to the sensor signal, an appropriate magnitude and/or phase of the time-varying electric current 242 to be provided to the cancellation coil 234 such that the resultant third time-varying magnetic field 232 at the antenna 224 destructively interferes with the first time-varying magnetic field 212 at the antenna 224. In certain implementations, the at least one sensor 246 is positioned at or near the antenna 224 such that the sensor signal is indicative of the first time-varying magnetic field 212 at or near the antenna 224, and the control circuitry 248 is configured to use the sensor signal as a feedback signal to optimize (e.g., "zero out") the first time-varying magnetic field 212 at or near the antenna 224 while the first time-varying magnetic field 212 elsewhere is configured to provide the desired amount of power transfer.

In certain implementations, the at least one fourth circuit 240 comprises at least a portion of the at least one first circuit 210. For example, instead of the at least one sensor 246 of FIG. 2G, at least a portion of the at least one first circuit 210 can be configured to generate a signal indicative of the first time-varying magnetic field 212 and to provide the signal to the control circuitry 248 of the fourth circuit 240. The control circuitry 248 can be configured to respond to the signal by generating (e.g., actively) the time-varying electric current 242. In certain such implementations, the third time-varying magnetic field 232 and the first time-varying magnetic field 212 have the same frequency content (e.g., the same phase and the same shape) as one another. The magnitude of the third time-varying magnetic field 232 can be adjusted (e.g., optimized) by controlling (e.g., limiting) the time-varying electric current 242 provided to the at least one third circuit 230 (e.g., by controlling the gain of an amplifier; by using a series resistance; etc.).

Figure 5:
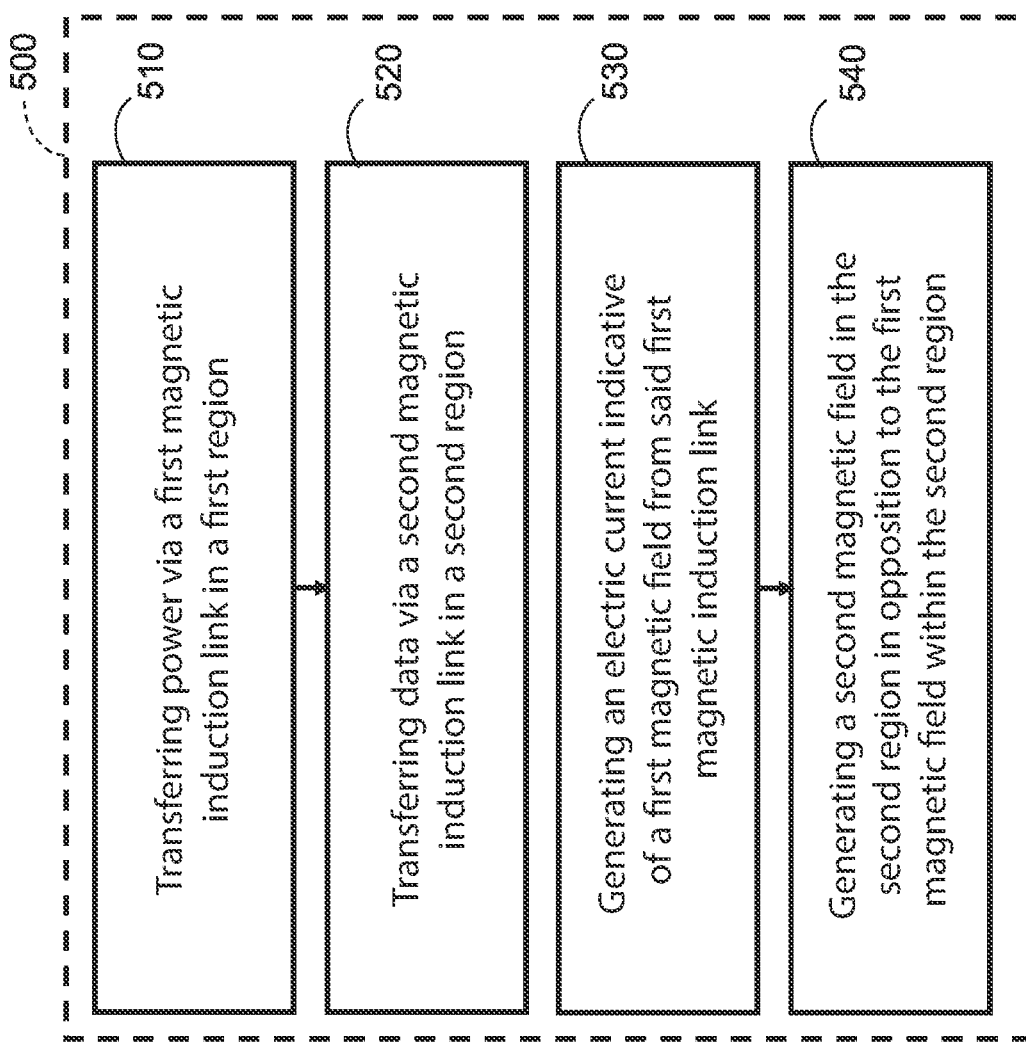
FIG. 5 is a flow diagram of an example method in accordance with certain implementations described herein.

FIG. 5 is a flow diagram of an example method 500 in accordance with certain implementations described herein. In an operational block 510, the method 500 comprises transferring power via a first magnetic induction link in a first region. For example, the first magnetic induction link can utilize the at least one first circuit 210 (e.g., energizing the first magnetic induction link by transmitting electric current along the power transfer coil 214 to transfer power via magnetic induction to a corresponding circuit).

In an operational block 520, the method 500 further comprises transferring data via a second magnetic induction link in a second region, the data transfer simultaneous with the power transfer. For example, the second magnetic induction link can energize the at least one second circuit 220 (e.g., transmitting electric current along the antenna 224) at the same time that the first magnetic induction link is energized. In certain implementations, the second region is within the first region (e.g., the power transfer coil 214 encircles the antenna 224), while in certain other implementations, the second region is separate from the first region (e.g., the power transfer coil 214 does not encircle the antenna 224; the antenna 224 is alongside the power transfer coil 214).

In an operational block 530, the method 500 further comprises generating an electric current indicative of a first magnetic field from the first magnetic induction link. In certain implementations, the electric current is generated by the at least one fourth circuit 240. For example, the electric current can be magnetically induced in the pick-up coil 244 (e.g., using the first magnetic field to magnetically induce the electric current in the pick-up coil 244). For another example, the electric current can be generated by magnetically inducing a sensor signal (e.g., using a sensor coil 246) indicative of the first magnetic field and using circuitry (e.g., control circuitry 248) to generate the electric current in response to the sensor signal.

In an operational block 540, the method 500 further comprises generating, in response to the electric current, a second magnetic field in the second region in opposition to at least a portion of the first magnetic field within the second region. In certain implementations, the second magnetic field is generated via magnetic induction by causing the electric current (e.g., generated by the at least one fourth circuit 240) to flow in a path bounding the second region. For example, the electric current can flow along the at least one third circuit 230 (e.g., cancellation coil 236), with the second magnetic field within the second region (e.g., bounded by the cancellation coil 236) in opposition to the first magnetic field along a direction substantially perpendicular to the cancellation coil 236. In certain implementations, the second magnetic field is configured to destructively interfere with at least a portion of the first magnetic field within the second region. For example, the second magnetic field can substantially totally destructively interfere with the first magnetic field substantially perpendicular to a plane of the cancellation coil 236 in the second region (e.g., substantially complete cancellation of the Z component of the net magnetic field).

Figure 6A:
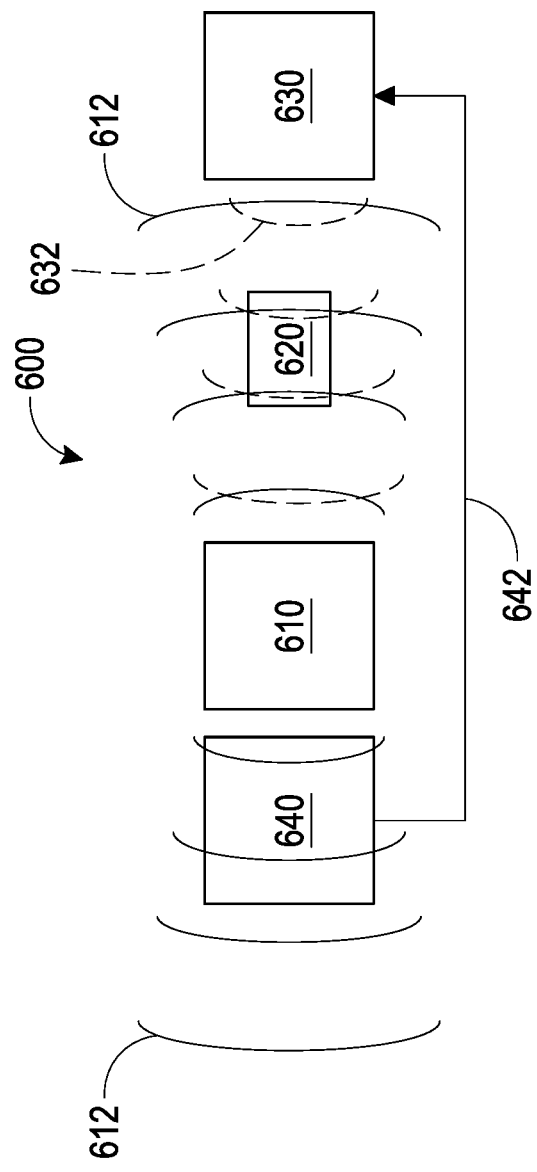
FIGS. 6A-6B schematically illustrate two example apparatus configured to reduce degradation of various types of low-power systems that are sensitive to magnetic fields in accordance with certain implementations described herein.
Figure 6B:
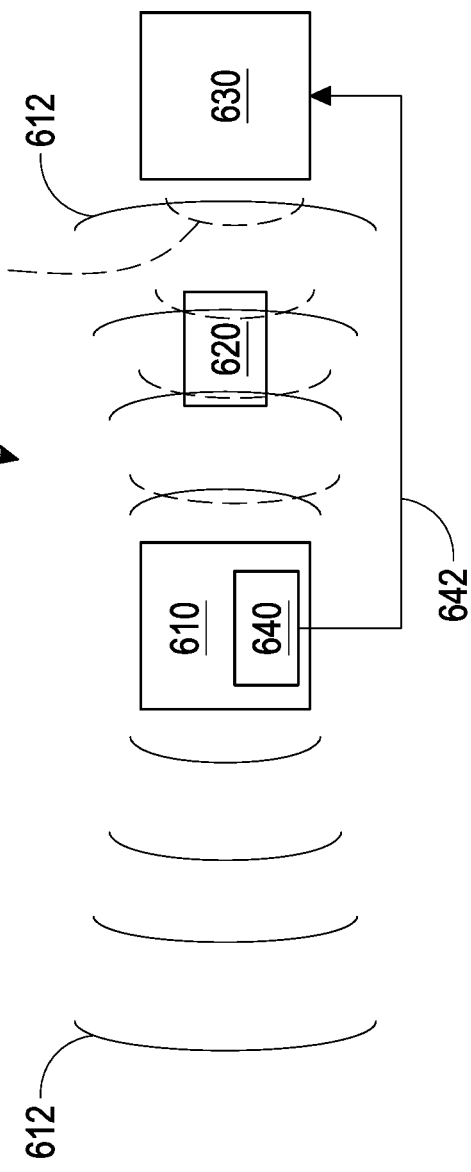

FIGS. 6A-6B schematically illustrate two example apparatus 600 configured to reduce degradation of various types of low-power systems that are sensitive to magnetic fields in accordance with certain implementations described herein. For example, certain implementations of the apparatus 200 of FIGS. 2A-2G as described herein can reduce degradation of a low-power magnetic induction data transfer link due to a nearby high-power magnetic induction power transfer link.

The apparatus 600 comprises magnetic induction power transfer circuitry 610 (e.g., at least one first circuit 210) configured to generate an induction power transfer magnetic field 612 (e.g., the first time-varying magnetic field 212). The apparatus 600 further comprises at least one circuit 620 (e.g., at least one second circuit 220) that is sensitive to the induction power transfer magnetic field 612. The apparatus 600 further comprises protection circuitry 630 (e.g., at least one third circuit 230) configured to generate a protection magnetic field 632 (e.g., the third time-varying magnetic field 232) in response to an electric current 642 (e.g., the time-varying electric current 242). The protection magnetic field 632 is configured to at least partially protect the at least one circuit 620 from the induction power transfer magnetic field 612. The apparatus 600 further comprises circuitry 640 (e.g., the at least one fourth circuit 240) configured to generate the electric current 642 in response to the induction power transfer magnetic field 612 or in response to a signal indicative of the induction power transfer magnetic field 612. In certain implementations, the at least one circuit 620 comprises at least one antenna 224 of a data transfer link (e.g., as described above with regard to FIGS. 2A-2G). As schematically illustrated in FIG. 6A, the circuitry 640 can be separate from the magnetic induction power transfer circuitry 610. As schematically illustrated in FIG. 6B, the circuitry 640 can comprise at least a portion of the magnetic induction power transfer circuitry 610.

In certain implementations, the at least one circuit 620 comprises a sensor in various contexts (e.g., medical devices; consumer devices; IoT devices; vehicles) that is sensitive to interference from the induction power transfer magnetic field 612 of the magnetic induction power transfer circuitry 610 of the device. For example, the sensor can be a microphone of an auditory prosthesis device or of any other device (e.g., consumer device; IoT device) in which the microphone is vulnerable to magnetic interference from the magnetic induction power transfer circuitry 610 of the device.

It is to be appreciated that the implementations disclosed herein are not mutually exclusive and may be combined with one another in various arrangements. In addition, although the disclosed methods and apparatuses have largely been described in the context of conventional cochlear implants, various implementations described herein can be incorporated in a variety of other suitable devices, methods, and contexts. More generally, as can be appreciated, certain implementations described herein can be used in a variety of implantable medical device contexts that can benefit from a signal pathway between the stimulation assembly and the recipient during implantation (e.g., insertion) of the stimulation assembly.

Language of degree, as used herein, such as the terms "approximately," "about," "generally," and "substantially," represent a value, amount, or characteristic close to the stated value, amount, or characteristic that still performs a desired function or achieves a desired result. For example, the terms "approximately," "about," "generally," and "substantially" may refer to an amount that is within ±10% of, within ±5% of, within ±2% of, within ±1% of, or within ±0.1% of the stated amount. As another example, the terms "generally parallel" and "substantially parallel" refer to a value, amount, or characteristic that departs from exactly parallel by ±10 degrees, by ±5 degrees, by ±2 degrees, by ±1 degree, or by ±0.1 degree, and the terms "generally perpendicular" and "substantially perpendicular" refer to a value, amount, or characteristic that departs from exactly perpendicular by ±10 degrees, by ±5 degrees, by ±2 degrees, by ±1 degree, or by ±0.1 degree.

The invention described and claimed herein is not to be limited in scope by the specific example implementations herein disclosed, since these implementations are intended as illustrations, and not limitations, of several aspects of the invention. Any equivalent implementations are intended to be within the scope of this invention. Indeed, various modifications of the invention in form and detail, in addition to those shown and described herein, will become apparent to those skilled in the art from the foregoing description. Such modifications are also intended to fall within the scope of the claims. The breadth and scope of the invention should not be limited by any of the example implementations disclosed herein, but should be defined only in accordance with the claims and their equivalents.

What is claimed is:

1. An apparatus comprising:
   at least one first circuit configured to generate and/or receive a first time-varying magnetic field for magnetic induction data transfer to and/or from a device;
   at least one second circuit configured to generate a second time-varying magnetic field in response to a time-varying electric current, the second time-varying magnetic field configured to at least partially inhibit degradation of said data transfer from a third time-varying magnetic field; and at least one third circuit configured to generate the time-varying electric current in response to a received portion of the third time-varying magnetic field or in response to a signal indicative of the third time-varying magnetic field.

2. The apparatus of claim 1, wherein the at least one first circuit comprises at least one antenna and the at least one second circuit comprises at least one cancellation coil bounding a region containing the at least one antenna.

3. The apparatus of claim 1, wherein the at least one third circuit comprises at least one pick-up coil in series electrical communication with the at least one second circuit, the at least one pick-up coil configured to passively generate the time-varying electric current via magnetic induction resulting from the received portion of the third time-varying magnetic field.

4. The apparatus of claim 3, further comprising at least one power transfer coil configured to generate the third time-varying magnetic field, the at least one power transfer coil having a first projection in a projection plane, the at least one pick-up coil having a second projection in the projection plane, the second projection within the first projection.

5. The apparatus of claim 3, further comprising at least one power transfer coil configured to generate the third time-varying magnetic field, the at least one power transfer coil having a first projection in a projection plane, the at least one pick-up coil having a second projection in the projection plane, the second projection outside the first projection.

6. The apparatus of claim 4, wherein projections of the at least one first circuit and the at least one second circuit in the projection plane are outside the first projection.

7. The apparatus of claim 6, wherein the at least one pick-up coil comprises a plurality of pick-up coils in series electrical communication with the at least one second circuit.

8. The apparatus of claim 1, wherein the at least one third circuit comprises at least one sensor coil and control circuitry in series electrical communication with the at least one second circuit, the at least one sensor coil configured to passively generate a sensor signal via magnetic induction resulting from the received portion of the third time-varying magnetic field, the control circuitry configured to respond to the sensor signal by actively generating the time-varying electric current.

9. The apparatus of claim 1, wherein the apparatus comprises an external first portion of a medical system and the device comprises a second portion of the medical system implanted on or within a recipient.

10. The apparatus of claim 9, further comprising a housing containing at least one fourth circuit configured to generate the third time-varying magnetic field, the at least one first circuit, the at least one second circuit, and the at least one third circuit, the housing configured to be positioned externally to the recipient at least said data transfer.

11. The apparatus of claim 9, wherein said data transfer is transcutaneous.

12. The apparatus of claim 9, wherein the medical system comprises an auditory prosthesis system.

13. A method comprising:
generating an electric current indicative of a first magnetic field from a first magnetic induction link in a first region;
transferring data via a second magnetic induction link in a second region, said transferring data simultaneous with said generating the electric current; and
in response to the electric current, generating a second magnetic field in the second region in opposition to at least a portion of the first magnetic field within the second region.

14. The method of claim 13, wherein generating the second magnetic field comprises causing the electric current to flow in a path bounding the second region.

15. The method of claim 14, wherein generating the electric current comprises using the first magnetic field to magnetically induce the electric current.

16. The method of claim 14, wherein generating the electric current comprises magnetically inducing a sensor signal indicative of the first magnetic field and using circuitry to generate the electric current in response to the sensor signal.

17. The method of claim 13, wherein the second region is within the first region.

18. The method of claim 13, wherein the second region is separate from the first region.

19. The method of claim 13, wherein the second magnetic field is configured to destructively interfere with at least a portion of the first magnetic field within the second region.

20. An apparatus comprising:
at least one circuit that is sensitive to a first magnetic field;
protection circuitry configured to generate a protection magnetic field in response to an electric current, the protection magnetic field configured to at least partially protect the at least one circuit from the first magnetic field; and
circuitry configured to generate the electric current in response to the first magnetic field or in response to a signal indicative of the first magnetic field.

21. The apparatus of claim 20, wherein the at least one circuit comprises at least one antenna of a data transfer link.

22. The apparatus of claim 20, wherein the at least one circuit comprises a microphone sensitive to interference from the first magnetic field.

* * * * *